United States Patent [19]

Bartl et al.

[11] Patent Number: 4,732,860
[45] Date of Patent: Mar. 22, 1988

[54] PROCESS FOR DETERMINING THE PERKALLIKREIN CONTENT AND THE PARTIAL THROMBOPLASTIN TIME OF A PLASMA SAMPLE

[75] Inventors: Knut Bartl, Wilzhofen; Helmut Lill, Wielenbach, both of Fed. Rep. of Germany

[73] Assignee: Boehringer Mannheim GmbH, Mannheim-Waldhof, Fed. Rep. of Germany

[21] Appl. No.: 822,364

[22] Filed: Jan. 24, 1986

[30] Foreign Application Priority Data

Feb. 8, 1985 [DE] Fed. Rep. of Germany ....... 3504405

[51] Int. Cl.$^4$ ................. G01N 21/78; G01N 33/86; C12Q 1/56
[52] U.S. Cl. ................................. 436/34; 435/13; 436/69
[58] Field of Search ............ 436/69, 34; 435/13

[56] References Cited

U.S. PATENT DOCUMENTS 4,016,042  0/0000  Svendsen .
4,480,030  10/1984  Svendsen ............................. 435/13
4,508,644  4/1985  Heber et al. ................. 260/112.5 L

FOREIGN PATENT DOCUMENTS 2915310  10/1980  Fed. Rep. of Germany ........ 435/13
3311287  10/1984  Fed. Rep. of Germany ........ 436/69

OTHER PUBLICATIONS

Egberg et al., Chemical Abstracts, vol. 91, Abstract No. 189054p, 1979.
Schousboe, Blood, vol. 66, No. 5, pp. 1086-1091, Nov. 1985.
Kluft, J. Lab. Clin. Med., vol. 91, No. 1, pp. 83-95, 1978.
"Activated Thromobofax Reagent-Optimized" Instruction Sheet by Ortho Diagnostic Systems, Inc. 1980.
Ito et al., Clinical Chemistry, vol. 27, No. 4 Apr. 1981, pp. 586-593.
H. U. Bergmeyer "Methods of Enzymatic Analysis", Third Edition, pp. 411-414, 1983.
Fareed et al., Clinical Chemistry, vol. 29, No. 2, Feb. 1983, pp. 225-236.
Chemical Abstracts, vol. 93, No. 23, Abstract No. 93:217028v 8 Dec. 1980, p. 202.
Chemical Abstracts, vol. 92, No. 19, Abstract No. 92:159405g p. 205.

Primary Examiner—Michael S. Marcus
Assistant Examiner—Robert J. Hill, Jr.
Attorney, Agent, or Firm—Felfe & Lynch

[57] ABSTRACT

The present invention provides a process for the photometric determination of prekallikrein in plasma, wherein plasma is incubated with a surface activator, the extinction obtained is measured, a chromogenic thrombin substrate is then added thereto, the optically determinable group liberated therefrom is measured at short time intervals or continuously and the gradient of the linear part of the curve obtained by plotting the time against the extinction is determined as a measure of the prekallikrein content. The partial thromboplastin time of plasma is simultaneously determined by carrying out the incubation in the presence of calcium ions and a phospholipid and measuring the time it takes the extinction to reach a predetermined level.

9 Claims, 3 Drawing Figures

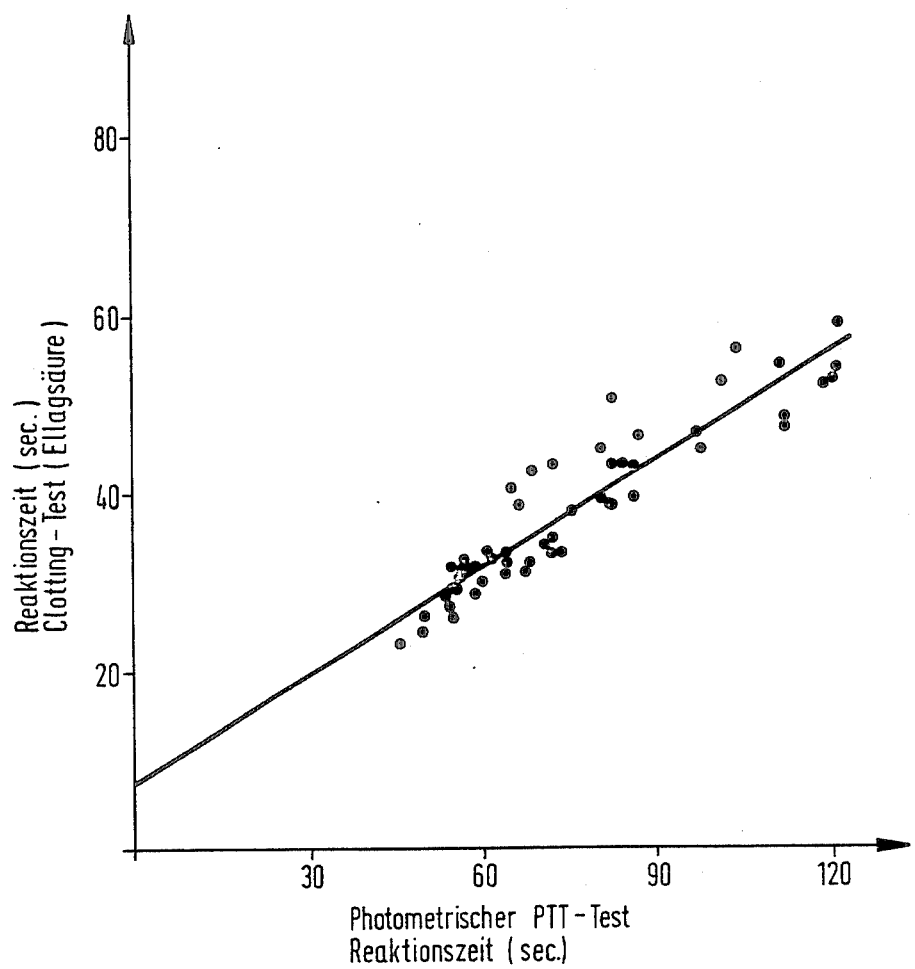

PROCESS FOR DETERMINING THE PERKALLIKREIN CONTENT AND THE PARTIAL THROMBOPLASTIN TIME OF A PLASMA SAMPLE

The present invention is concerned with a process for the determination of prekallikrein.

Statements regarding the blood coagulation system can be made from the determination of prekallikrein. The absence of prekallikrein manifests itself in a prolonged coagulation time. In the case of prolonged coagulation times, the prekallikrein determination can give conclusions whether this prolongation is caused by a deficiency of Factor VIII or IX or by a prekallikrein deficiency. If the prekallikrein determination shows that there is a deficiency of Factor VIII or IX, then this indicates serious diseases. Furthermore, in the case of certain other diseased states, for example shock, a change of the amount of prekallikrein is acertained.

The formation of kallikrein from prekallikrein in the plasma takes place according to the following reactions:

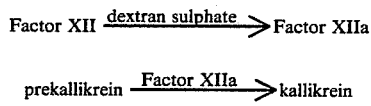

The known methods for the determination of prekallikrein are described in H. U. Bergmeyer's "Methods of enzymatic analysis", 3rd edition, Volume V, pp. 412-413. Besides some very complicated and time-consuming methods, which cannot be considered for a routine determination in the laboratory, it is also known to determine kallikrein formed after the activation of Factor XII with dextran sulphate via a chromogenic substrate. However, this process has the disadvantage that the incubation for the conversion of prekallikrein into kallikrein must be carried out at 0° C. in order to prevent the influence of plasma inhibitors, for example alpha$_1$-antitrypsin and C$_1$-inactivator, on the measurement result. The incubation at 0° C. in turn seriously hinders the automation of this process.

Therefore, it is an object of the present invention to provide a simple and rapid process for the determination of prekallikrein which does not suffer from the above-mentioned disadvantages and, in particular, can be carried out at normal temperatures.

Thus, according to the present invention, there is provided a process for the photometric determination of prekallikrein, wherein plasma is incubated with a surface activator, the extinction obtained is measured, a chromogenic thrombin substrate is then added thereto, the optically determinable group liberated therefrom is measured at short time intervals or continuously and the gradient of the linear part of the curve obtained by plotting the time against the extinction is determined as a measure of the prekallikrein content.

The surface activator is preferably ellagic acid, sulphatides (preferably from brain material) and finely-divided silicon dioxide, such as is commercially available, for example, as "Aerosil" (Degussa, Germany). Dextran sulphate is not suitable. Ellagic acid is especially preferably present in a concentration of 0.08 to 2.1 μg./ml. of test solution, the best results being obtained with a concentration of 0.40 to 0.45 μg. ellagic acid per ml. These and all the following statements of concentration in the description refer to the end concentration in the test.

Surprisingly, in the case of the process according to the present invention, it is possible to incubate at normal temperatures, especially at 20° to 40° C. and preferably at 30° to 37° C.

As chromogenic thrombin substrates, there can be used the commercially available peptides for this purpose which contain a chromogenic group, especially a p-nitroaniline group or a derivative thereof, which, by the action of an enzyme, is split off from the substrate and can then be determined optically. Preferred chromogenic thrombin substrates for use within the scope of the present invention include Tos-Gly-Pro-Arg-pNA, H-D-CHA-Ala-Arg-pNA, H-D-CHG-Gly-Arg-pNA, H-D-CHG-Ala-Arg-pNA, H-D-CHG-but-Arg-pNA, naphthyl-SO$_2$-Gly-Pro-Arg-pNA, and H-D-Phe-Pip-Arg-pNA. The abbreviations used herein will be recognized by one skilled in the art as standing for the following: "Tos" stands for p-toluenesulfonyl, "Gly" stands for glycine, "Pro" stands for proline, "Arg" stands for arginine, "pNA" stands for p-nitroanilide, "D-CHA" stands for D-3-cyclohexylalanine, "Ala" stands for L-alanine, "D-CHG" stands for D-2-cyclohexylglycine, "but" stands for L-2-aminobutyric acid, "D-Phe" stands for D-phenylalanine, and "Pip" stands for pipecolic acid.

The concentration of the chromogenic thrombin substrate is preferably 0.01 to 2 mMol/l., depending upon the Michaelis constant of the substrate in question. As substrate, it is especially preferred to use Tos-Gly-Pro-Arg-p-nitroaniline in a concentration of about 0.2 mMol/l.

According to a special embodiment of the process according to the present invention, this can be carried out in such a manner that it makes possible a simultaneous determination of prekallikrein and of the partial thromboplastin time (PTT). In this case, a substrate must be used which is sufficiently sensitive for the PTT determination, such as the above-mentioned Tos-Gly-Pro-Arg-pNA. In the case of such a simultaneous determination, the concentration of the chromogenic thrombin substrate can be reduced and is then usually about 0.02 to 0.04 mMol/l. The reduction of the concentration is for measurement-technical reasons in order that, in the recording of the S-shaped curve, the swing of the recorder is not too great.

The process according to the present invention is preferably carried out in the presence of animal, vegetable or synthetic phospholipids. Examples of suitable phospholipids include cephalin, soya bean phospholipid, phosphatidylethanolamine and phosphatidylcholine. However, numerous other phospholipids can also be used but, because of the large number thereof, they are not specially mentioned here. Cephalin is especially preferred, the amount thereof preferably being from 4 to 200 μg./ml. In the case of a simultaneous determination of PTT, an addition of a phospholipid is essential.

Furthermore, it is preferable to carry out the process according to the present invention in the presence of calcium ions since the addition of calcium brings about an increase of the extinction difference per unit time. A concentration of 1 to 100 μmol/ml. calcium ions can be used, a concentration of 25 to 40 μmol/ml. calcium ions being preferred. In the case of the simultaneous determination, the addition of calcium ions is necessary. In the case of the addition of calcium ions and of phospholipid, there is obtained an S-shaped curve, the base line of which is used for the prekallikrein determination.

In the case of the process according to the present invention, the incubation time is from 1 to 10 minutes, 4 to 6 minutes being preferred. In the case of too long or too short incubation times, lower prekallikrein values are obtained.

In the scope of the present invention, as plasma there can be used, for example, citrate plasma, oxalate plasma or EDTA plasma.

If the process according to the present invention is carried out in the presence of calcium ions, then the measurement takes place in about the first 30 seconds after addition of the plasma since the extinction subsequently increases steeply. Without the addition of calcium ions, this steep increase does not occur and the measurement can also be carried out in longer intervals of time.

The formation of the chromophore from the chromogenic substrate is monitored photometrically. This can take place not only kinetically by determination of the extinction changes per unit time but also by a two-point kinetic as well as by end point measurement. In the case of an end point measurement, the colour formation reaction must be stopped, which preferably takes place by the addition of acid. Thus, for example, acetic acid or citric acid are especially suitable for stopping. In the case of acetic acid, this is preferably used in a concentration of 20 to 100 vol.% and in the case of citric acid in a concentration of 5 to 20 vol.%.

BRIEF DESCRIPTION OF THE DRAWINGS

The following Examples are given for the purpose of illustrating the present invention, reference thereby being made to the accompanying drawings, in which:

FIG. 3 is a graphic representation which shows the correlation of the PTT determination in the simultaneous test with the present invention with a known PTT test process.

EXAMPLE 1

Determination of prekallikrein

Reagent 1:
buffer (tris/HCl): 100 μmol/ml., pH 7.6
ellagic acid: 0.5 μg./ml.
cephalin from rabbit brain: 0.04 mg./ml.
merthiolate: 0.01% by wt.
Reagent 2:
Tos-Gly-Pro-Arg-pNA 0.376 μmol/ml.

Figure 1:
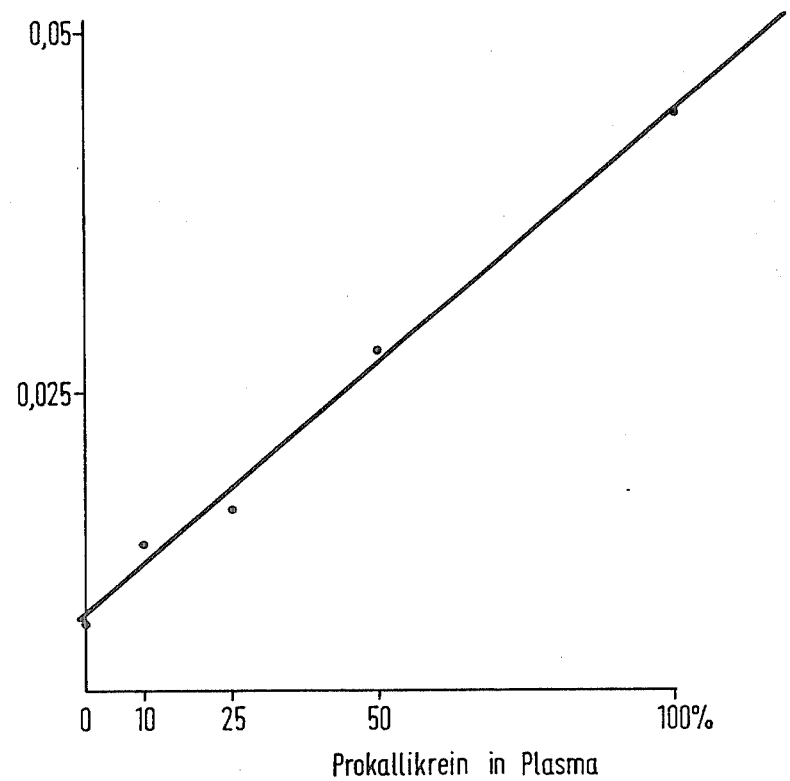
FIG. 1 is a graphic representation of the extinction difference per unit time in the case of differing prekallikrein contents in the plasma.

0.2 ml. of sample (citrate plasma) is added to 2.0 ml. of Reagent 1 and incubated for 5 minutes at 37° C. Subsequently, 0.2 ml. of Reagent 2 is added thereto, mixed and a photometric determination carried out immediately at 37° C. and 405 nm. In the case of different prekallikrein contents in the plasma, as a result there are obtained the measurement values according to FIG. 1. In this case, 100% prekallikrein in the plasma means the prekallikrein content of a normal plasma pool.

EXAMPLE 2

Addition of calcium ions 0.2 ml. of sample (citrate plasma) is added to 2.0 ml. of Reagent 1 (Example 1, ±cephalin) and the mixture incubated at 37° C. for 5 minutes. Subsequently 0.2 ml. of Reagent 2 (Tos-Gly-Pro-Arg-pNA, 0.376 μmol/ml., with and without calcium ions 40 μmol/ml.) is added thereto.

The determination is carried out in the manner described in Example 1. In the case of the addition of calcium ions, ΔE/min. must be measured within the course of the first 25 seconds.

The following Table I shows the influence of calcium ions or cephalin on the sensitivity of the test:

TABLE I

| cephalin | + | − | + | − |
|---|---|---|---|---|
| $Ca^{2+}$ | + | + | − | − |
| ΔE/min. | 0.04 | 0.03 | 0.036 | 0.028 |

EXAMPLE 3

Determination of prekallikrein in the presence of silicon dioxide

In Reagent 1 of Example 1, instead of ellagic acid there is added 1 mg./ml. of "Aerosil" 200. In the presence of 40 μmol/ml. calcium ions, there is obtained ΔE/min. = 0.04.

EXAMPLE 4

Simultaneous determination of prekallikrein and PTT

Reagent 1:
analogous to Example 1
Reagent 2:
Tos-Gly-Pro-Arg-pNA: 0.376 μmol/ml.
calcium ions: 40 μmol/ml.

Figure 2:
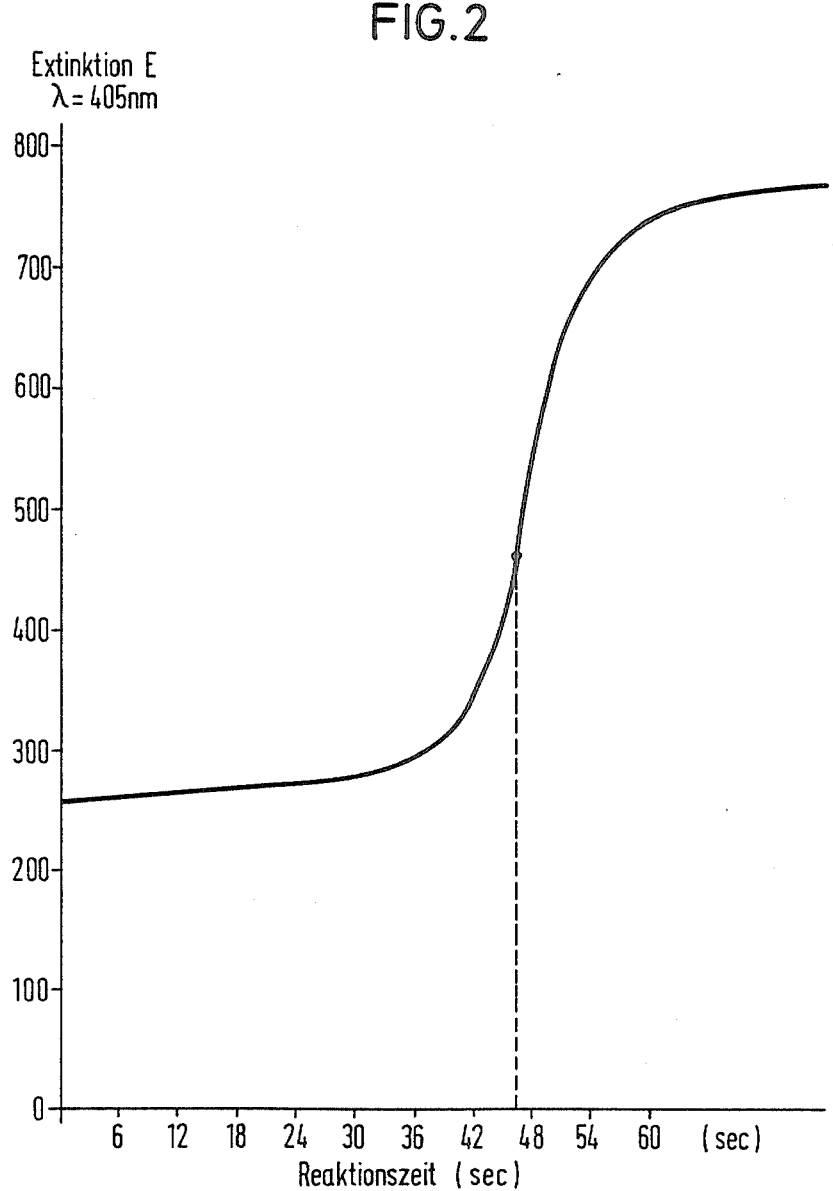
FIG. 2 is a graphic representation of the extinction plotted against the reaction time, from which can be seen the S-shaped course of the curve.

The carrying out of the test takes place analogously to Example 1, ΔE/min. being determined within 25 seconds for the determination of prekallikrein. Thereafter, the reaction is allowed to continue and a "fixed absorbance measurement" is carried out, the time up to the achievement of a definite extinction difference to the blank value (ΔE=0.2) thereby being measured. This time is the PTT time. FIG. 2 of the accompanying drawings shows the course of the extinction recorded with a recorder (PTT time: 46.3 seconds; prekallikrein reaction: 0.042 ΔE/min.).

FIG. 3 of the accompanying drawings shows the correlation of the PTT determination according to Example 4 with a conventional PTT test. (Clotting method, Actin test, Merz and Dade). It follows therefrom that the PTT determination is not disturbed by the prekallikrein test.

What is claimed is:

1. Process for the simultaneous photometric determination of the prekallikrein content of a plasma sample and the partial thromboplastin time of said sample comprising incubating a plasma sample with a surface activator along with calcium ions and a phospholipid to form a reaction mixture, measuring the extinction of the reaction mixture, adding a chromogenic substrate specific to thrombin to the reaction mixture, measuring an optically determinable group liberated from the chromogenic substrate in the reaction mixture by measuring the extinction of the reaction mixture at short time intervals or continuously, said incubation taking place at a temperature of from 20° to 40° C., and simultaneously determining a gradient of a linear part of a curve obtained by plotting time against the extinction of the reaction mixture as a measure of the prekallikrein content of the plasma sample and the partial thromboplastin time by measuring the time it takes the extinction of the reaction mixture to reach a predetermined level.

2. The process of claim 1, wherein the chromogenic thrombin substrate is selected from the group consisting of Tos-Gly-Pro-Arg-pNA, H-D-CHA-Ala-Arg-pNA, H-D-CHG-Gly-Arg-pNA, H-D-CHG-Ala-Arg-pNA, H-D-CHG-but-Arg-pNA, naphthyl-SO$_2$-Gly-Pro-Arg-pNA, and H-D-Phe-Pip-Arg-pNA.

3. The process of claim 1, wherein incubation is carried out at 30° to 37° C.

4. The process of claim 1 wherein incubation is carried out for 1 to 10 minutes.

5. The process of claim 1, wherein the calcium ions are present in the reaction mixture in a concentration of 1 to 100 μmol/ml.

6. The process of claim 1 wherein the surface activator is ellagic acid, a sulphatide or finely-divided silicon dioxide.

7. The process of claim 6, wherein the surface activator is 0.08 to 2.1 μg of ellagic acid per ml of reaction mixture.

8. The process of claim 1, wherein the phospholipid is cephalin, soya bean, phospholipid, phosphatidylethanolamine or phosphatidylcholine.

9. The process of claim 8, wherein the phospholipid is 4 to 200 μg cephalin per ml of reaction mixture.

* * * * *